United States Patent [19]

Starr

[11] Patent Number: 5,560,487
[45] Date of Patent: Oct. 1, 1996

[54] HOLDER AND PACKAGING FOR BIOPROSTHETIC HEART VALVE

[75] Inventor: Stephen Starr, Austin, Tex.

[73] Assignee: CarboMedics, Inc., Austin, Tex.

[21] Appl. No.: 282,675

[22] Filed: Jul. 29, 1994

[51] Int. Cl.[6] .................................................. A61B 17/06
[52] U.S. Cl. ........................... 206/438; 206/363; 206/583
[58] Field of Search .................................... 206/438, 363, 206/583, 439, 305

[56] References Cited

U.S. PATENT DOCUMENTS

| D. 345,910 | 4/1994 | Millwee et al. | D9/418 |
|---|---|---|---|
| 4,101,031 | 7/1978 | Cromie | 206/438 |
| 4,182,446 | 1/1980 | Penny | 206/205 |
| 4,211,325 | 7/1980 | Wright | 206/438 |
| 4,512,471 | 4/1985 | Kaster et al. | 206/438 |

Primary Examiner—Paul T. Sewell
Assistant Examiner—Tara L. Laster
Attorney, Agent, or Firm—John R. Merkling

[57] ABSTRACT

A heart valve holder and packaging for supporting a bioprosthetic heart valve. The holder is attached to the heart valve, preferably with a single suture, and has a grip for either direct manual manipulation of the heart valve or for the attachment of a removable handle. A clip is provided which attaches to the heart valve holder and suspends the valve holder and the heart valve within a casing or jar. Ethanol or another suitable fluid within the jar protects the heart valve from biologic contamination, while the structure of the heart valve holder and clip protect the heart valve from physical damage. The valve holder, with attached heart valve, and the clip, can be removed from the jar as a single unit, and the clip can be detached from the heart valve holder.

18 Claims, 4 Drawing Sheets

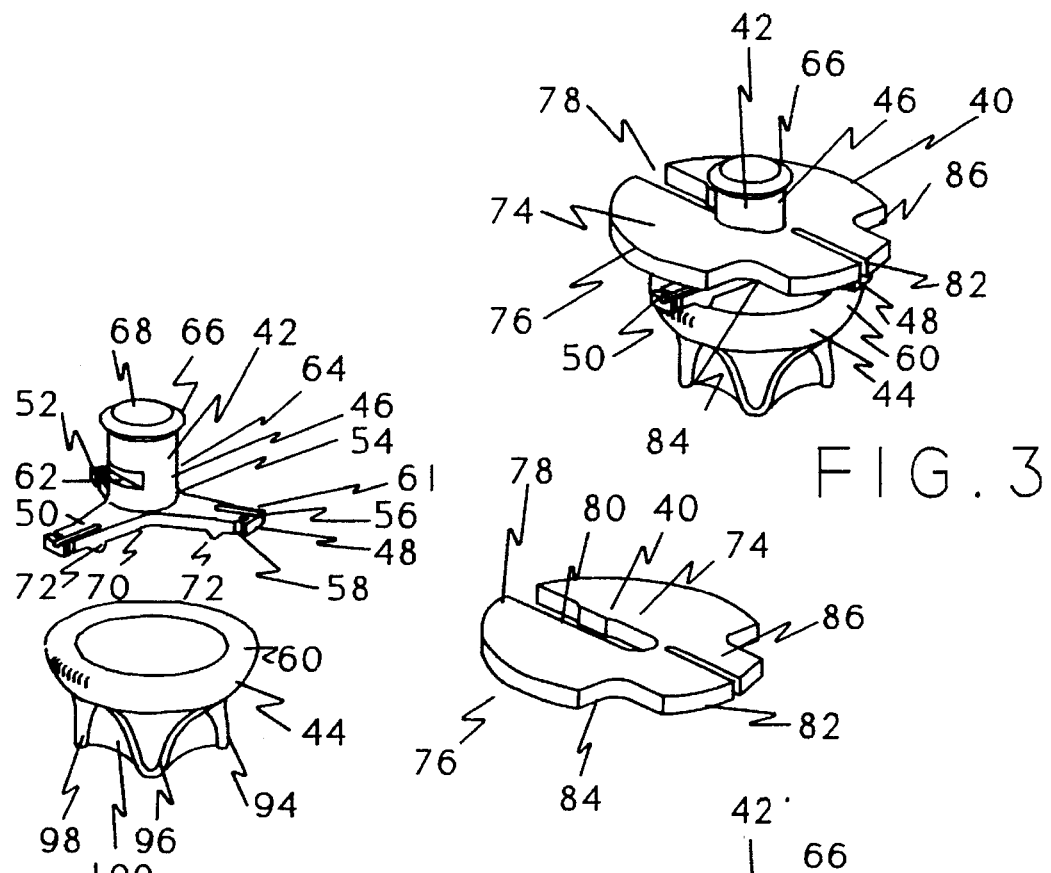
FIG. 3
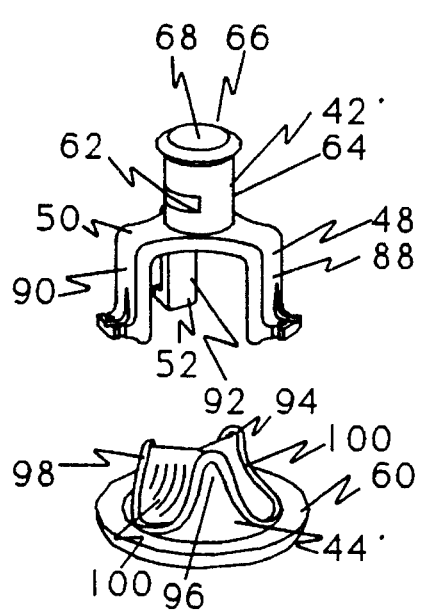
FIG. 4
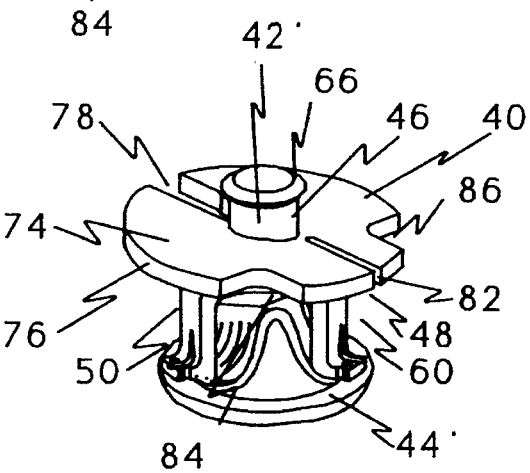
FIG. 5
FIG. 6

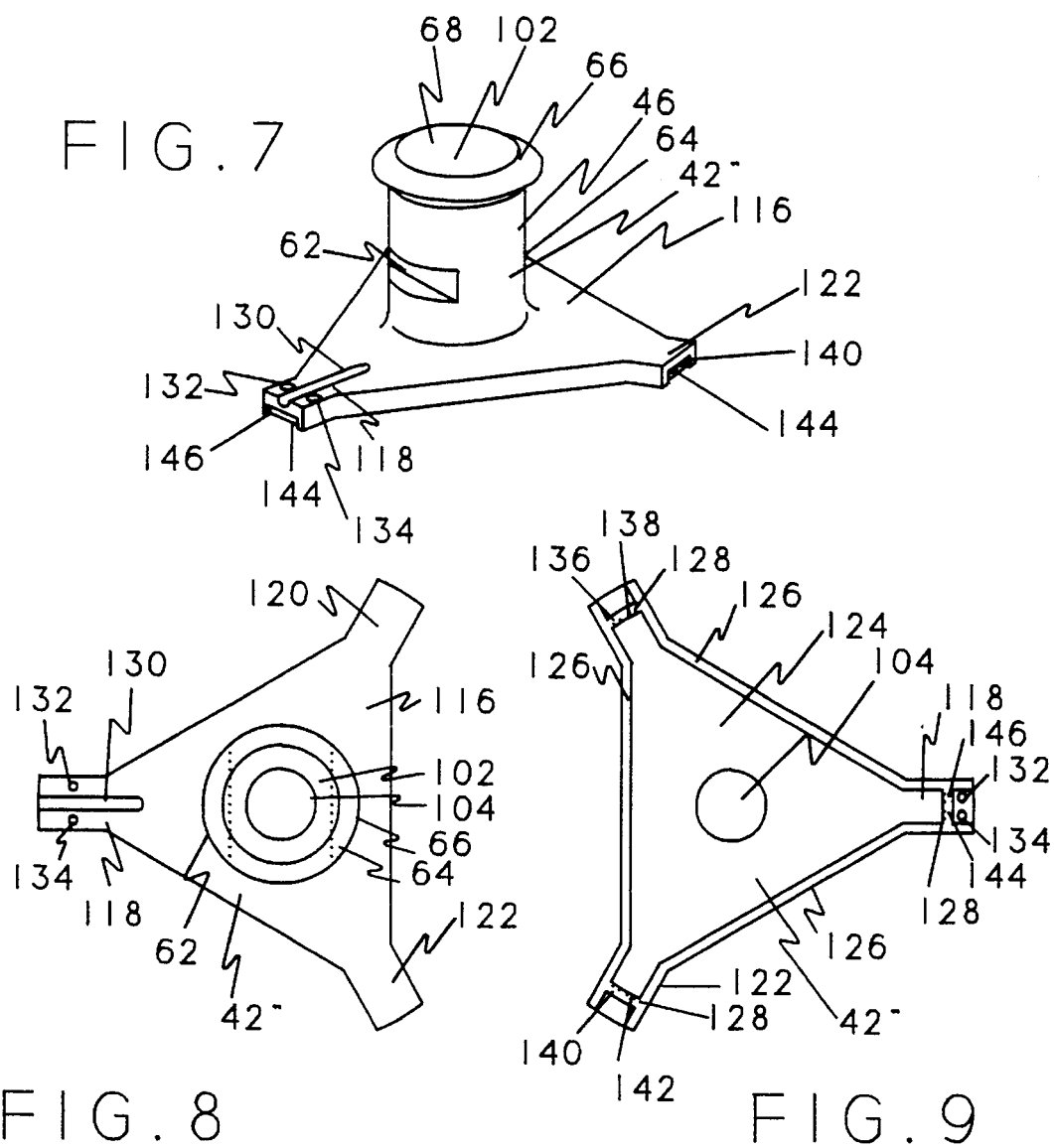

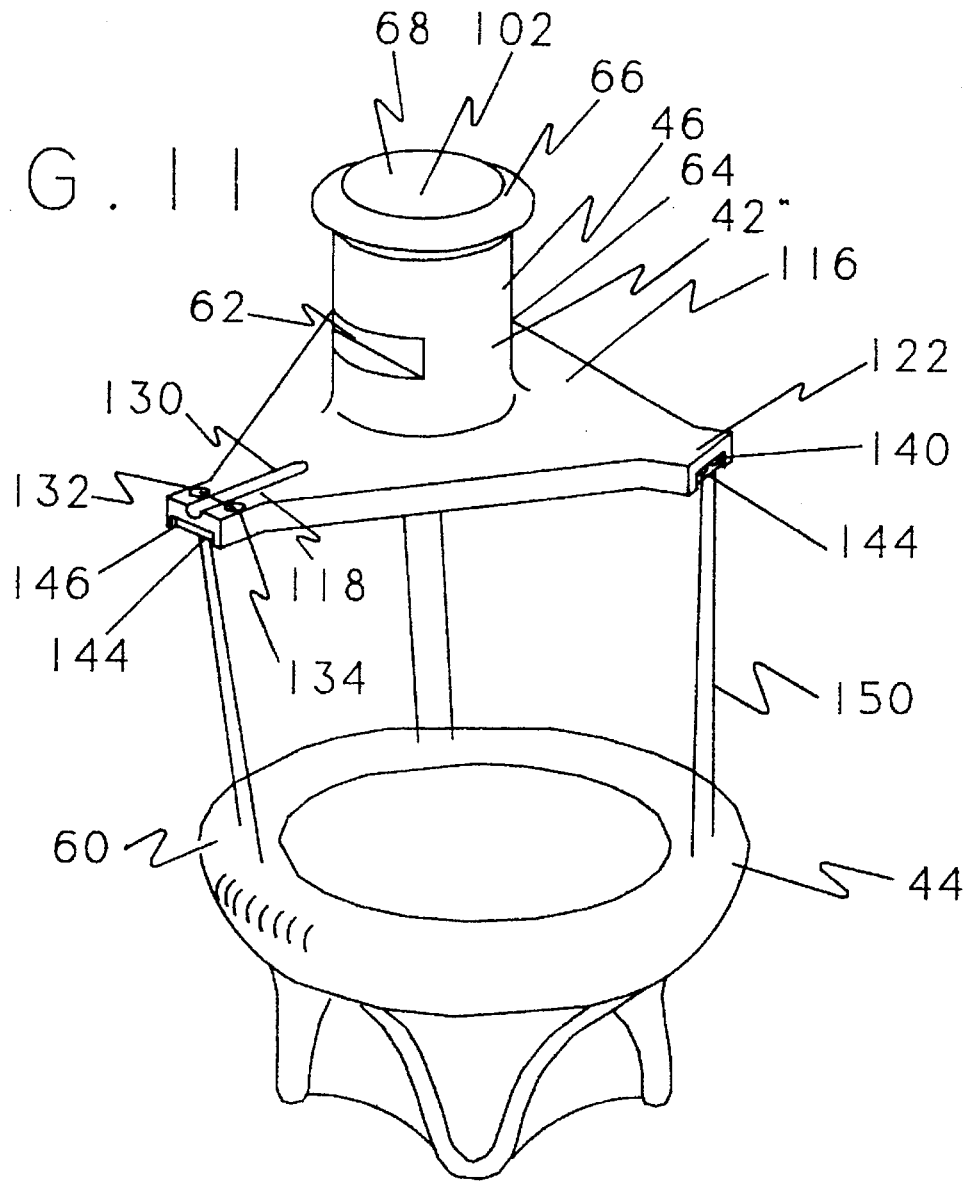

5,560,487

HOLDER AND PACKAGING FOR BIOPROSTHETIC HEART VALVE

FIELD OF MY INVENTION

My invention relates to heart valve holders and packaging for bioprosthetic heart valves, and particularly to a heart valve holder which is retained within packaging by a clip.

BACKGROUND OF MY INVENTION

Prosthetic heart valves, used to replace diseased natural heart valves, fall generally into two categories. The first category comprises heart valves with relatively rigid leaflets. These valves have 1, 2 or 3 leaflets formed of a stiff biocompatible substance, such as pyrolytic carbon. These valves, sometimes called "mechanical" valves, are often designed to have two leaflets pivoting in an rigid annulus, such as the design shown in U.S. Pat. No. 4,888,010 to Bokros.

The second category of prosthetic heart valves, called "bioprosthetic" valves, comprises valves with flexible leaflets, frequently made of a biological material. This second category can also be divided broadly into two classes. The first class comprises bioprosthetic heart valves typically including a wire stent frame with three flexible leaflets attached thereto. An example of such a valve is disclosed by Lane in U.S. Pat. No. 5,037,434, which is assigned to the assignee of my invention. These heart valves imitate the natural action of heart valves and so provide a structure which is relatively compatible with the cardiovascular system.

The second class of bioprosthetic heart valves do not have a stent or frame. They have the advantage of being constructed from flexible material, but they can be collapsed and deformed by the action of the heart.

Both classes of bioprosthetic heart valves are frequently constructed using biologic materials. Such materials are environmentally sensitive, and it is usual to protect the integrity of the valve from both impacts and contamination. Packaging for such valves has been provided wherein the valve floats or is retained within a bath of an appropriate fluid, such as ethanol. The packaging remains sealed until it is opened in the surgical theater, where implantation in a patient's heart is to take place. It is important, therefore, for packaging to provide an appropriate structure that can be easily manipulated both to protect the heart valve and to allow the valve to be implanted more easily and without risk of infection.

SUMMARY OF MY INVENTION

I have invented a heart valve holder and packaging for supporting a bioprosthetic heart valve. The holder is attached to the heart valve, preferably with a single suture, and has a grip for either direct manual manipulation of the heart valve or for the attachment of a removable handle. A clip is provided which attaches to the heart valve holder and suspends the valve holder and the heart valve within a casing or jar. Ethanol or another suitable fluid within the jar protects the heart valve from biologic contamination, while the structure of the heart valve holder and clip protect the heart valve from physical damage. The valve holder, with attached heart valve, and the clip, can be removed from the jar as a single unit, and the clip can be easily detached from the heart valve holder.

With the foregoing in mind it is an object of mine invention to provide a heart valve holder and associated packaging which protects a prosthetic heart valve.

It is a further object of my invention to provide a heart valve holder with an easily removable clip which supports the holder and attached heart valve within a protective jar.

Another object of my invention is to provide a heart valve holder which is attached to a heart valve with a single suture.

Another important object of my invention is to provide a heart valve holder which can be manipulated easily either by direct hand manipulation or through a detachable handle.

These and other objects and features of my invention will be apparent from the following detailed description taken with reference to the accompanying drawings.

BRIEF DESCRIPTION OF THE DRAWINGS

FIG. 3 is a perspective view of a valve holder for a mitral valve with a support clip attached.

FIG. 4 is an exploded perspective view of the mitral heart valve and holder of FIG. 3.

FIG. 5 is a perspective view of an aortic valve and heart valve holder.

FIG. 6 is an exploded perspective view of the heart valve and holder of FIG. 5.

FIG. 7 is a perspective view of my preferred embodiment of a heart valve holder, with provision for attaching the heart valve to the holder with a single suture.

FIG. 8 is a top plan view of the valve holder in FIG. 7

FIG. 9 is a bottom plan view of the heart valve holder of FIG. 7

FIG. 10 is a detachable handle suitable for use with any of the heart valve holders shown in FIGS. 3, 5, and 7.

FIG. 11 is a perspective view of the valve holder of FIG. 7 with a heart valve and suture.

DETAILED DESCRIPTION OF MY PREFERRED EMBODIMENT

I will now explain my invention with reference to the accompanying drawings wherein like numerals designate like parts throughout.

Figure 1:
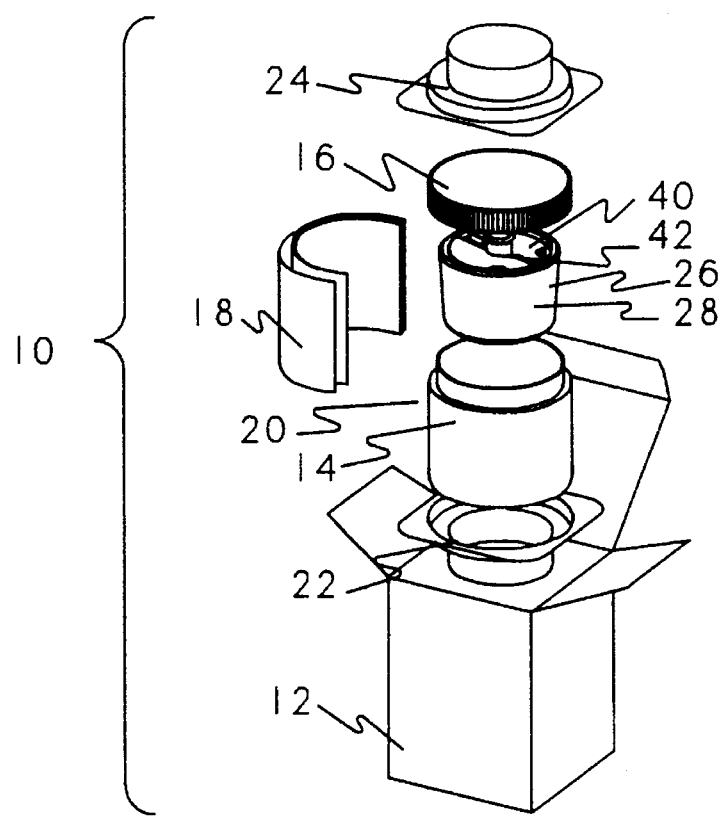
FIG. 1 is an exploded perspective view of a heart valve holder and packaging for a bioprosthetic heart valve according to my present invention.

FIG. 1 illustrates a perspective exploded view of a heart valve packaging system, generally designated 10, according to my invention. The system 10 comprises an outer box 12 which contains a sealable jar 14 with a lid 16. The lid 16 is threadedly received on the jar 14 so as to contain an appropriate fluid, such as ethanol. As is known in the art, labeling 18 may be applied to an outside surface 20 of the jar 14. In addition, of course, labeling would also typically be applied to the box 12. The jar is supported within the box by a bottom package support 22 which is inserted into the box 12 and supports the jar. A top package support 24 is placed over the lid. The two package supports 22, 24 support the jar within the box 12, but space it away from the outside walls, thus providing increased protection against physical damage to the jar 14.

Figure 2:
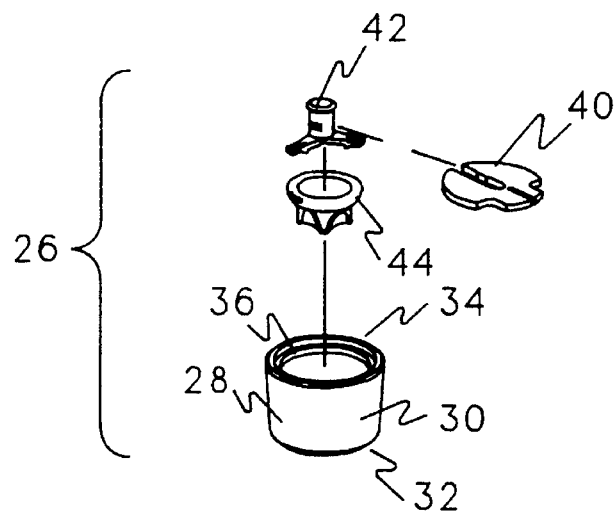
FIG. 2 is an exploded perspective view of the valve holder and a valve holder retainer.

Within the jar 14 is a valve holder retainer 26. The holder retainer 26 can best be described by reference to FIG. 2, where it is shown in exploded perspective view. The holder retainer 26 comprises a casing 28 having an outer circumferential wall 30. A bottom may be provided at a bottom edge 32 of the circumferential wall 30, but is preferably omitted. Adjacent an upper edge 34, a shelf 36 extends circumferentially around the inside of the wall 30. This shelf 36 receives a support clip 40. The support clip 40 fastens to a valve holder 42, as will be more particularly described below. The valve holder 42 supports a heart valve 44. The heart valve 44 is stitched to the heart valve holder 42 with sutures. With the heart valve holder mounted in the clip 40 and the clip resting of the shelf 36, the heart valve is completely supported away from the surrounding walls of either the casing 28 or the jar 14.

The form and function of the heart valve holder 42 and the clip 40 can best be understood by reference of the embodiments of FIGS. 3 through 9. FIGS. 3 and 4 illustrate a mitral heart valve 44 with an appropriate heart valve holder 42 and clip 40. The heart valve holder comprises a central post 46 with three radially extending arms 48, 50, 52 at a distal end 54 of the post 46. On each arm 48, 50, 52, there are provided means for suturing the heart valve 44 to the holder. On each arm I have illustrated a through bore 56 and a slot 58 for securing a suture (not shown) through a sewing ring 60, a known feature of bioprosthetic heart valves. The suture should pass over a grove 61 in the arm so that a surgeon can cut the suture with a scalpel, freeing the heart valve from the holder. The heart valve holder also has two slots 62, 64 on the post 42. These slot 62, 64 cooperate with the clip 40 to support the heart valve 44. The valve holder 42 also has a lip 66 at a proximal edge 68 thereof. By gripping the post and lip 66, a surgeon would be able to manipulate the heart valve holder, and consequently the heart valve, with little difficulty. On a distal side 70 of the arms, a transverse ridge 72 may be provided to give additional support to the heart valve by fitting within the annulus formed by the sewing ring 60.

The clip 40 comprises a flat plate 74 having a peripheral edge 76 adapted to rest on the shelf 36. One will recognize that the shelf 36 may be affixed to a casing, as shown, but it may also be formed as a feature of the jar 14 and the casing 26 can be completely omitted without departing from the essential characteristics of my invention. The clip 40 has a first slot 38, which is wide enough to fit around the post of the valve holder 42 within the slots 62, 64. A tab 80 may be provided inside the slot for 78 to fasten the heart valve holder 42 essentially in the middle of the clip 40. A second slot 82 extends generally on the same line as the slot 78. On either side of the second slot 82 are indentations 84, 86 which provide finger grips. By pressing against the finger grips 84, 86 the attending physician can collapse the second slot 82 thus spreading the first slot 78 and permitting the clip 40 to be removed from the heart valve holder. The clip 40, therefore, must be both sufficiently rigid to support the heart valve holder and valve, but sufficiently flexible to allow the slot 78 to be enlarged. I have found that acetal copolymer available from Global Plastics, Inc. of Mavern, Pa., has suitable characteristics.

In contrast to FIGS. 3 and 4, FIGS. 5 and 6 illustrate an aortic heart valve 44' and an aortic heart valve holder 42'. The aortic heart valve holder 42' is different from the aortic valve holder 42 described above, in that the legs 48, 50, 52 each have an axial portion 88, 90, 92 which allows the valve holder 4' to be mounted over commissures 94, 96, 98 and valve leaflets 100 of the aortic valve 44'. In other respects, the holder 42' and clip 40 are as described above.

My presently preferred embodiment of a heart valve holder is illustrated in FIGS. 7 through 10. This embodiment can be used either for the aortic or the mitral valve and can be attached to the heart valve 44 using a single suture. This suture can than be cut at a single location and the heart valve holder removed from the heart valve. My preferred embodiment of the heart valve holder is shown at numeral 42" in perspective view in FIG. 7. As before, a central post 42 is provided with slots 62, 66 thereon. The post 46 has proximal lip 66 and a central bore 102. The bore 102 can best be seen in FIG. 8 and tapers down to a threaded through bore 104. I have also provided a removable handle 106, shown in plan view in FIG. 10, which can be attached to the heart valve holder using the threaded bore 104. The handle 106 comprises a head 108 having a distal threaded shaft 110. The threaded shaft 110 can be screwed into the threaded bore 104. The head 108 is connected by a shaft 112 to a hand grip 114. The shaft 112 is preferably metal and deformable so that the handle may be bent by the surgeon during use.

The heart valve holder 42" further comprises a triangular plate 116 at the distal end of the post 46. The features of the plate 116 can best be appreciated with reference to the top plan view of FIG. 8 and the bottom plan view of FIG. 9. The triangular plate 116 has arms 118, 120, 122, at each vertex of the triangle. On a distal side 124 of the plate 116, a peripheral edge or lip 126 is provided along the edges of the triangular plate 116. On the arms, a cross brace 128 is provided between the lips 126 and spaced radially inwardly from the ends of the arms. On one of the arms, for example, arm 118, a scalpel slot 130 is provided between two axial suture bore 132, 134. On each of the three arms 118, 120, 122 two radial suture bores 136, 138, 140, 142, 144, 146 are provided in the cross brace 128.

To attach the heart valve 44 to the heart valve holder 42", a suture 150 is tied in one of the radial suture bores farthest away from the arm 118 with the scalpel slot 130. This would be, for example, suture bore 140. The suture is then led down to the sewing ring 60 and stitched through the sewing ring. The suture is then led back up to the radial suture bore 142 and passed through that bore from the outside toward the center of the triangular plate, that is, in the direction of the threaded bore 104. The suture then is passed along the distal side of the plate and within the lip 126. The suture passes through a radial bore 144 and then down to the sewing ring 60 again. On its return, however, the suture is passed first through the axial suture bore 132, then across the scalpel slot 130 and back down the axial bore 134 before passing through another radial through bore 146. Thereafter, as before, the suture is led along the distal side of the triangular plate 116 but within the lip 126 to the last arm 120 where it is passed through the radial suture bore 138, then through the sewing ring 60 and returned to the final radial suture bore 136, where it is secured by tying, for example.

It will be apparent from the forgoing described method of suturing the heart valve holder, that a single suture secures the heart valve to the heart valve holder 42". A surgeon can cut the suture by passing a scalpel through the scalpel slot 130. The heart valve holder could then be withdrawn from the heart valve, removing the suture at one time.

My invention may be embodied in other specific forms without departing from the teachings or central characteristics thereof. The present embodiment is therefore considered in all respects to be illustrative and not restrictive, the scope of my invention being indicated by the appendant claims rather than by the foregoing description and all changes which come within the meaning and range within the equivalency of the claims are intended to be embraced therein.

I claim as my invention:

1. A packaging system for a bioprosthetic heart valve comprising a container for receiving said heart valve, said container having an interior surface defining a chamber, a heart valve holder to which said heart valve can be releasably attached, means for attaching said heart valve to said heart valve holder, a clip which releasably clasps said heart valve holder for supporting said holder within said container and having a plate with an edge configured to contact said interior surface of said chamber and a first slot for receiving a portion of said heart valve holder, and a lid removably mounted on said container to selectively enclose said heart valve holder and heart valve within said chamber.

2. The packaging system according to claim 1 wherein said plate further comprises a second slot, co-linear with said first slot, whereby compression of said second slot enlarges said first slot.

3. The packaging system according to claim 2 further comprising a ledge within said chamber for supporting said plate.

4. The packaging system according to claim 3 wherein said heart valve holder comprises post means for connecting with said first slot of said plate.

5. The packaging system according to claim 4 further comprising a handle selectively attached to said heart valve holder.

6. The packaging system according to claim 5 wherein said handle further comprises a bendable shaft.

7. The packaging system according to claim 6 further comprising a casing received within said chamber for providing said ledge within said chamber.

8. The packaging system according to claim 7 wherein said plate further comprises means for griping said plate to compress said second slot.

9. The packaging system according to claim 8 wherein said heart valve holder comprises a valve holder plate attached to a distal end of said post means, said valve holder plate having
an outer edge, and
a lip extending distally from said outer edge, and a plurality of arms extending radially outward from said valve holder plate, means for securing a suture means to a first arm, means for threading said suture means to at least a last arm, and means for securing said suture means to at least said last arm.

10. The packaging system according to claim 9 wherein said plurality of arms further comprise at least one middle arm between said first arm and said last arm, each arm having at least two through bores, said middle arm having a scalpel slot for guiding a scalpel to cut said suture means.

11. A heart valve holder to which a bioprosthetic heart valve can be releasably attached, said heart valve holder comprising post means for manipulating said heart valve holder, a valve holder plate attached to a distal end of said post means, said valve holder plate having
an outer edge, and
a lip extending distally from said valve holder plate, a plurality of arms extending radially outward from said outer edge of said valve holder plate, means for securing a suture means to a first arm, means for threading said suture means to at least a last arm, and means for securing said suture means to at least said last arm.

12. The heart valve holder according to claim 11 wherein said plurality of arms further comprise at least one middle arm between said first arm and said last arm, each arm having at least two through bores, said middle arm having a scalpel slot for guiding a scalpel to cut said suture means.

13. A bioprosthetic heart valve and packaging system therefor comprising a prosthetic heart valve having a central orifice and a circumferential sewing ring, a container for receiving said head valve, said container having an interior surface defining a chamber and a ledge within said chamber, a suture means a heart valve holder to which said heart valve can be releasably attached by said suture means, said heart valve holder having
post means,
a valve holder plate attached to a distal end of said post means, said valve holder plate having
an outer edge, and
a lip extending distally from said outer edge, and
at least a first arm, a middle arm and a last arm, said arms extending radially outward from said valve holder plate, each arm having at least two through bores, said middle arm having a slot for guiding a scalpel to cut said suture means, said suture means being secured in one bore in said first arm, stitched into said heart valve, passed through the other bore in said first arm, along said valve holder plate adjacent said lip, through a first bore in said middle arm, stitched into said heart valve, passed around said middle arm, through another bore in said middle arm, along said valve holder plate adjacent said lip, through a first bore in said last arm, stitched into said heart valve, and secured in another bore in said last arm a clip which releasably clasps said heart valve holder for supporting said holder within said container, said clip comprising
a plate having an edge configured to contact said ledge of said interior surface of said chamber,
a first slot for receiving a portion of said heart valve holder,
a second slot, co-linear with said first slot, whereby compression of said second slot enlarges said first slot, and a lid removably mounted on said container to selectively enclose said heart valve holder and heart valve within said chamber.

14. The bioprosthetic heart valve and packaging system according to claim 13 wherein said middle arm further has two bores adjacent said scalpel slot and wherein said suture means passes through said bores adjacent said scalpel slot and across said scalpel slot.

15. In combination, a bioprosthetic heart valve and heart valve holder to which said bioprosthetic heart valve can be releasably attached, said bioprosthetic heart valve having a central orifice and a circumferential sewing ring and said heart valve holder comprising post means for manipulating said heart valve holder, a valve holder plate attached to a distal end of said post, said plate having
an outer edge, and
a lip extending distally from said outer edge, and at least a first arm, a last arm and a middle arm between said first arm and said last arm, each arm having at least two through bores, said middle arm having a scalpel slot for guiding a scalpel, said arms extending radially outward from said valve holder plate, suture means secured in one bore in said first arm, stitched into said heart valve, passed through the other bore in said first arm, along said valve holder plate adjacent said lip, through a first bore in said middle arm, stitched into said heart valve, passed across said slot in said middle arm, through another bore in said middle arm, along said valve holder plate adjacent said lip, through a first bore in said last arm, stitched into said head valve, and secured in another bore in said last arm.

16. The heart valve and heart valve holder according to claim 15 wherein said middle arm further has two bores adjacent said scalpel slot and wherein said suture means passes through said adjacent bores and across said scalpel slot.

17. The heart valve and heart valve holder according to claim 16 further comprising a handle selectively attached to said heart valve holder.

18. The heart valve and heart vlalve holder according to claim 17 wherein said handle further comprises a bendable shaft.

* * * * *